United States Patent [19]

Mittelstadt et al.

[11] Patent Number: 5,562,655
[45] Date of Patent: Oct. 8, 1996

[54] SURGICAL APPARATUS HAVING A UNIVERSAL HANDLE FOR ACTUATING VARIOUS ATTACHMENTS

[75] Inventors: William A. Mittelstadt, Woodbury; Arthur V. Lang, Maplewood, both of Minn.

[73] Assignee: United States Surgical Corporation, Norwalk, Conn.

[21] Appl. No.: 289,681

[22] Filed: Aug. 12, 1994

[51] Int. Cl.$^6$ ..................................................... A61B 17/00
[52] U.S. Cl. .............................. 606/1; 606/205; 606/208
[58] Field of Search ................................. 606/1, 51, 52, 606/139, 142, 143, 144, 205–208; 128/749–754

[56] References Cited

U.S. PATENT DOCUMENTS

| | | |
|---|---|---|
| 3,086,208 | 4/1963 | Eby . |
| 3,638,847 | 2/1972 | Noiles . |
| 3,665,924 | 5/1972 | Noiles et al. . |
| 3,899,914 | 8/1975 | Akiyama . |
| 4,226,239 | 10/1980 | Polk et al. . |
| 4,393,883 | 7/1983 | Smyth et al. . |
| 4,430,997 | 2/1984 | DiGiovanni et al. . |
| 4,452,357 | 6/1984 | Klieman et al. . |
| 4,452,376 | 6/1984 | Klieman et al. . |
| 4,478,220 | 10/1984 | Di Giovanni et al. . |
| 4,500,024 | 2/1985 | DiGiovanni et al. . |
| 4,616,650 | 10/1986 | Green et al. . |
| 4,624,254 | 11/1986 | McGarry et al. . |
| 4,674,504 | 6/1987 | Klieman et al. . |
| 4,850,355 | 7/1989 | Brooks et al. . |
| 4,858,608 | 8/1989 | McQuilkin . |
| 5,030,226 | 7/1991 | Green et al. . |
| 5,040,715 | 8/1991 | Green et al. . |
| 5,084,057 | 1/1992 | Green et al. . |
| 5,100,420 | 5/1992 | Green et al. . |
| 5,104,394 | 4/1992 | Knoepfler . |
| 5,151,101 | 9/1992 | Grossi et al. . |
| 5,171,247 | 12/1992 | Hughett et al. ......................... 606/142 |
| 5,171,249 | 12/1992 | Stefanchik et al. . |
| 5,171,250 | 12/1992 | Yoon ........................................ 606/142 |
| 5,176,702 | 1/1993 | Bales et al. ............................. 606/205 |
| 5,190,541 | 3/1993 | Abele et al. ............................... 606/50 |
| 5,190,560 | 3/1993 | Woods et al. ........................... 606/142 |
| 5,192,288 | 3/1993 | Thompson et al. ..................... 606/143 |
| 5,207,691 | 5/1993 | Nardella . |
| 5,281,230 | 1/1994 | Heidmueller . |
| 5,282,800 | 2/1994 | Foshee et al. ........................... 606/208 |
| 5,282,808 | 2/1994 | Kovac et al. . |
| 5,287,807 | 2/1994 | Knoepfler . |
| 5,289,963 | 3/1994 | McGarry et al. . |
| 5,300,081 | 4/1994 | Young et al. . |
| 5,314,424 | 5/1994 | Nicholas . |
| 5,336,238 | 8/1994 | Holmes et al. ......................... 606/208 |
| 5,356,064 | 10/1994 | Green et al. . |
| 5,364,002 | 11/1994 | Green et al. . |
| 5,382,254 | 1/1995 | McGarry et al. . |
| 5,382,255 | 1/1995 | Castro et al. . |
| 5,389,098 | 2/1995 | Tsuruta et al. ......................... 606/142 |
| 5,403,312 | 4/1995 | Yates et al. ............................... 606/50 |

FOREIGN PATENT DOCUMENTS

| | | |
|---|---|---|
| 0588584 | 3/1994 | European Pat. Off. . |
| 0598529A2 | 5/1994 | European Pat. Off. . |
| 0605254 | 7/1994 | European Pat. Off. . |
| WO8403827 | 10/1984 | WIPO . |
| WO90/03763 | 4/1990 | WIPO . |

*Primary Examiner*—Angela D. Sykes
*Assistant Examiner*—Michael Peffley

[57] ABSTRACT

The present invention is embodied in a surgical apparatus that can be used in laparoscopic surgical procedures. In particular, the apparatus includes a universal actuating handle for use with different end effectors and that can convert a single handle motion into two separate and independent actuator motions required for actuating two separate actuating members. The handle also includes a collar that facilitates the connection and disconnection of the end effector to and from the handle in a single translational snap-on or snap-off motion. The handle also has a ratchet and pawl mechanism to provide improved control over actuation.

36 Claims, 11 Drawing Sheets

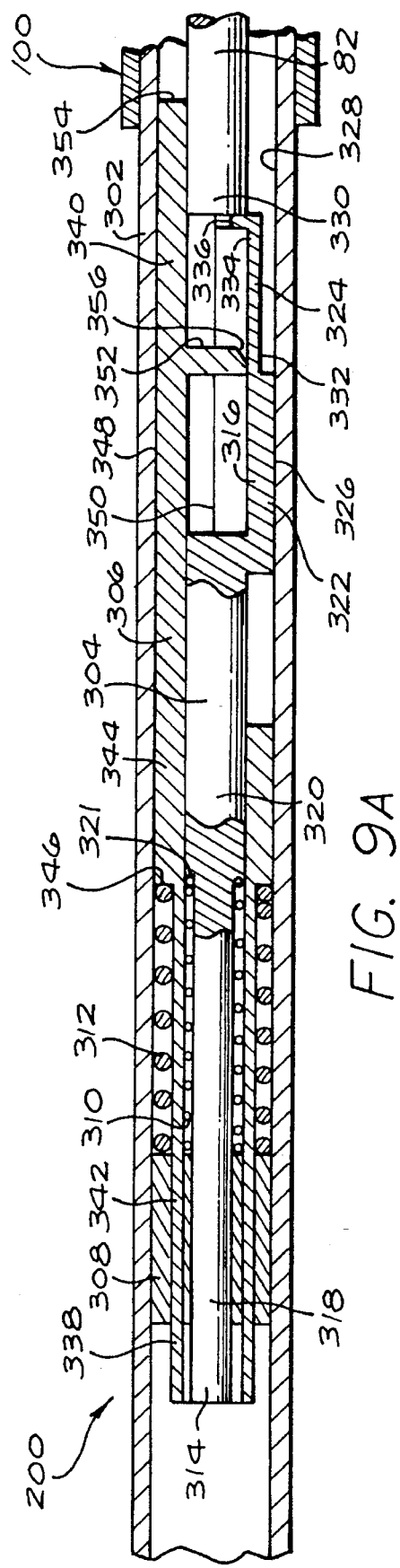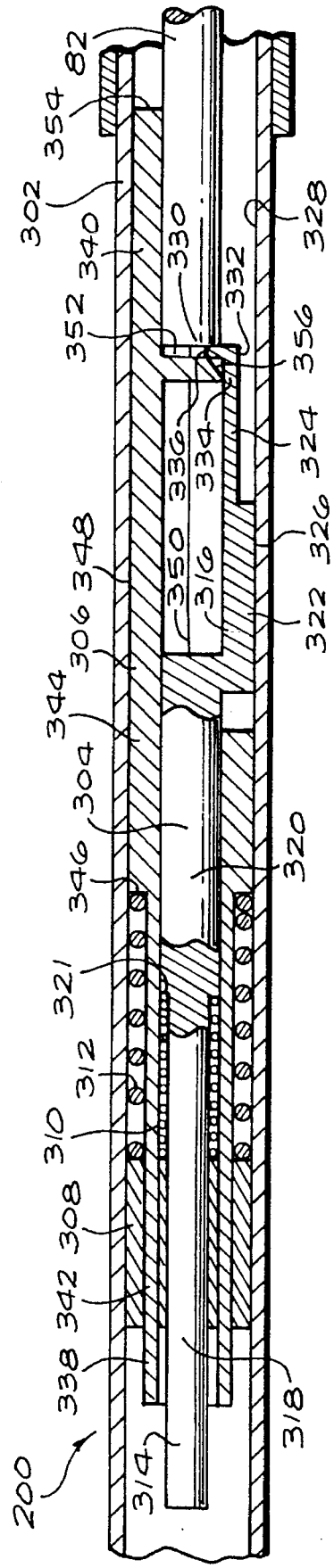
FIG. 9A
FIG. 9B

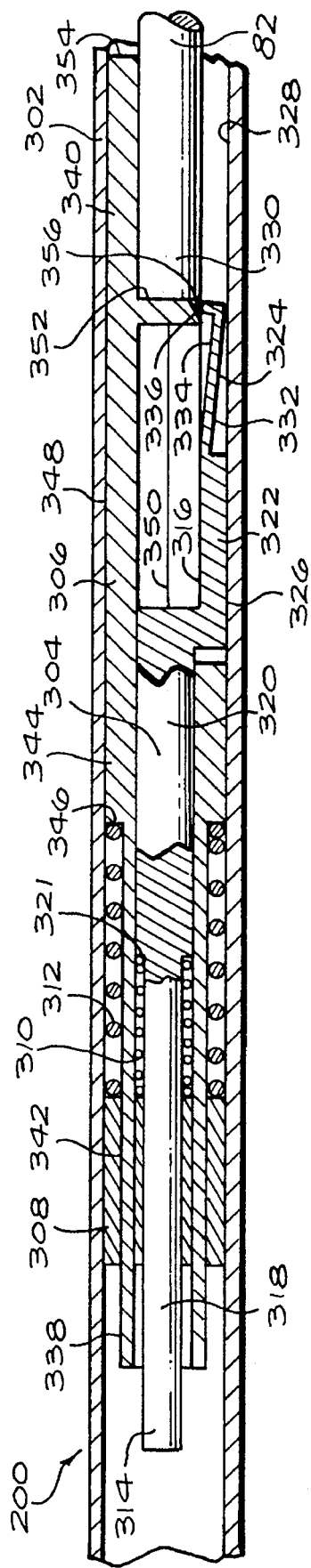
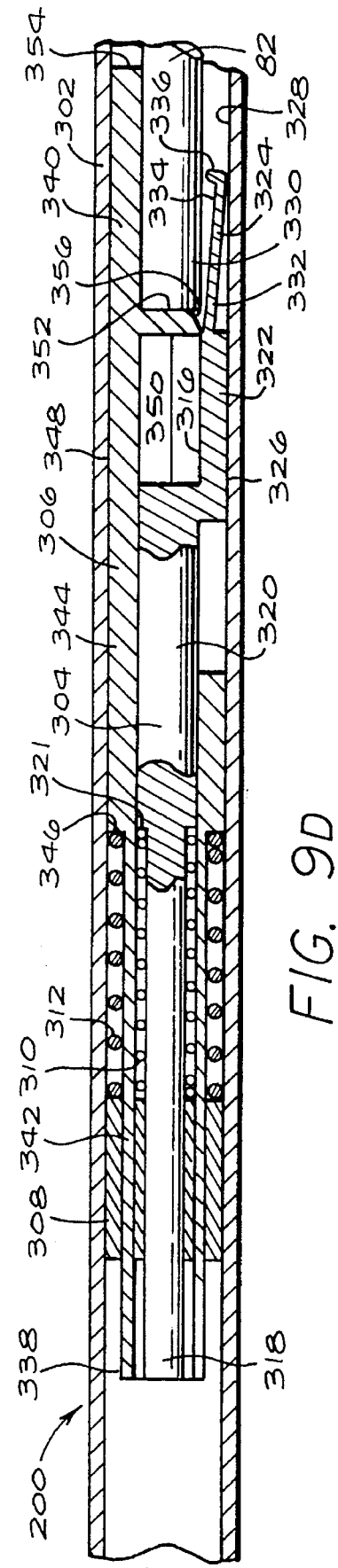
FIG. 9C
FIG. 9D

SURGICAL APPARATUS HAVING A UNIVERSAL HANDLE FOR ACTUATING VARIOUS ATTACHMENTS

The present invention relates generally to surgical instruments, and more particularly, to an instrument for use in laparoscopic surgical procedures, in which the instrument includes a universal handle that can actuate various different types of attachments.

BACKGROUND OF THE INVENTION

In laparoscopic procedures, surgery is performed in the abdomen through a small incision in the skin. Such procedures typically involve distending the abdominal cavity away from the underlying organs to improve access and visibility, using gas insufflation or a mechanical distension technique. Laparoscopic procedures generally require the surgeon to act on organs, tissues and vessels at a distance from the incision, thereby requiring that any instruments used in such procedures be long and narrow while being functionally controllable from the proximal end of the instrument.

Many different procedures may be performed during laparoscopic surgery requiring the use of many different instruments, such as, ligating clip appliers, staplers, disposable scissors and tackers. Presently, however, no universal handle is available to operate all of these varied instruments. Thus, hospital inventory is increased, instrument costs to hospitals are increased, the number of handles which require cleaning is increased, and the number of instruments present on the surgical tool table is increased. Additionally, the surgeon must become familiar with the operation of each of the different instruments, some of which have a plurality of triggers for actuating the different operating mechanisms of that instrument.

For example, in laparoscopic surgical procedures, it is frequently necessary to ligate ducts, such as blood vessels, or other severed tissues. For this purpose, it is well-known to use surgical clip appliers that advance a clip and clamp a clip, such as that described in U.S. Pat. No. 5,084,057. However, such a clip applier discloses the use of two actuating triggers, one to advance the clip and the other to clamp the clip. The dual trigger clip applier does not provide the ease of use and simplicity that accompanies the use of a single trigger instrument. In addition, the costs of manufacturing such a clip applier are increased since a handle with two triggers requires the additional molding and manufacture of a second trigger, associated trigger parts and additional lockouts.

Known laparoscopic instruments for applying surgical clips and which have a single actuating trigger include those devices disclosed in U.S. Pat. Nos. 5,289,963; 5,192,288; 5,171,249; and 5,171,247. The clip applier of U.S. Pat. No. 5,289,963, however, only has a movable clip advance mechanism, not a movable clamping mechanism. Therefore only one actuating trigger is necessary. The clip appliers of U.S. Pat. Nos. 5,192,288; 5,171,249; and 5,171,247 disclose devices having both movable clip advance and movable clamping mechanisms. The two mechanisms, however, do not operate independently, but rather are operated simultaneously as the trigger is actuated. Also, in each of these three patents, a clip is automatically advanced upon release of the trigger after the previous clip has been clamped. Therefore, the operator has less control of the clip feed and there is a chance that the clip may accidentally shoot out of the device or get caught or snagged by frictional forces so that the clip cannot advance.

In the case of a clip applier, it is also desirable that only one clip be fed into the jaws of the device at a time. For example, in previously known instruments, a ratchet and pawl mechanism was used to prevent the trigger from returning to the clip reload position until the previously loaded clip had been clamped to a duct. In one instrument, described in U.S. Pat. No. 5,289,963, the ratchet and pawl mechanism is mounted to a longitudinally movable plunger that actuates the operating mechanisms. In this case, however, the ratchet and pawl mechanism has the disadvantage of preventing the surgeon from reclosing the jaws of the device should the surgeon desire to confirm that the clip has been properly clamped. In another instrument, described in U.S. Pat. No. 5,192,288, the ratcheting mechanism includes a hooked end of the pawl that engages a grooved path of ridges and cliffs on the trigger. However, this ratcheting mechanism has a complex construction, and it may be unreliable since one must rely on the resiliency of the pawl to engage the grooved path.

It is also desirable in some instances to have a "resposable" instrument, i.e. an instrument having a disposable end effector detachable from a reusable handle. Most laparoscopic instruments are either fully disposable or fully reusable. Single use disposable instruments, however, are often not cost effective, whereas reusable instruments require thorough cleaning and sterilization between uses. U.S. Pat. No. 5,040,715 discloses the use of a detachable end effector having a finger structure for engaging an internal portion of the handle and having a movable sleeve for disengaging the end effector from the handle. However, the finger structure and sleeve make the end effector relatively expensive since additional molding and manufacturing are required. Also, tight tolerances are required to insure a secure fit between the attachment and the handle. Being disposable, the end effector should be as simple and inexpensive as possible.

Other known laparoscopic instruments have attachment devices for connecting and disconnecting various end effectors. However, these attachment devices are typically quick connect attachments that require that a knob be depressed as an end effector is attached. Another commonly known attachment means used with laparoscopic instruments is the bayonet mount. However, the bayonet mount requires an additional rotational motion, and if the rotational motion is not performed, the end effector cannot be securely attached. These attachment devices thus require additional manipulation, such as a coordinated, two-handed movement, to attach the end effector to the handle.

From the discussion above, it should be apparent that there is a need for a surgical apparatus that can be used in laparoscopic procedures and that includes a universal actuating handle for use with a variety of attachments or end effectors and that can convert a single lever motion of the handle into two separate and independent actuator motions. In addition, there is a need for a surgical apparatus that includes a ratchet and pawl mechanism for preventing the return of the actuating trigger so that only one clip is fed at a time, but that permits reclosure of the trigger to insure that the function of the end effector is properly performed. In addition, there is a need for a surgical apparatus having a disposable end effector that includes an attachment mechanism for connecting and disconnecting the end effector to and from a reusable handle that has a simple, secure and easy to use design requiring no additional manipulation or rotational motions, and that is economical and easy to manufacture.

SUMMARY OF THE INVENTION

The present invention is embodied in a surgical apparatus that can be used in laparoscopic surgical procedures. In particular, the apparatus includes a universal actuating handle that can be used with many different end effectors, including double action end effectors that can perform two functions and single action end effectors that perform a single function. The apparatus also converts a single lever motion of the handle into two separate and independent actuator motions for actuating two separate actuating members of the end effector. The apparatus also includes an attachment device for securely connecting and disconnecting the end effector to and from the handle in a single translational snap-on or snap-off motion. The handle includes a ratchet and pawl mechanism that insures that only one clip is fed into the jaws of a clip applier at a time, while permitting the surgeon to reclose the jaws, if necessary, during actuator return.

The surgical apparatus of the present invention includes a handle, a collar and an end effector. A plunger is mounted to the handle and has a distal end that moves longitudinally relative to the end effector. A first actuating member is located within the end effector and is in contacting longitudinal alignment with the plunger such that the plunger can engage the first actuating member and move it distally. A second actuating member is also located within the end effector and also is in contacting longitudinal alignment with the plunger such that after the plunger moves the first actuating member distally, the plunger engages the second actuating member and moves it distally.

A feature of the present invention is that the first actuating member includes a deflectable portion and the second actuating member includes a transverse wall. The deflectable portion and transverse wall are positioned in contacting alignment relative to each other such that distal movement of the first actuating member results in the transverse wall urging the deflectable portion out of longitudinal alignment with the plunger.

An advantage of this surgical apparatus is that it converts a single lever motion of the handle into two separate and independent motions for actuating the first actuating member and the second actuating member. For example, in an application where the actuating handle is used with an end effector for applying surgical clips to a duct or blood vessel, the single actuator of the present invention allows an operator to separately control the advancement of the clip and the closure of the clip around the duct or blood vessel. Also, by converting the motion in the end effector, the mechanical complexity of the handle is greatly simplified, without significantly increasing the complexity of the end effector.

Another advantage of the present invention is that the actuating handle can be used with various conventional end effectors, such as, ligating clip appliers, disposable scissors, staplers, and tackers, and is not limited to use with one specific end effector. Because the handle can be used with a variety of different end effectors, the advantages of the present invention include reducing hospital inventory, reducing instrument costs to hospitals, reducing the number of handles which require cleaning, reducing the number of instruments present on the surgical tool table, and reducing the number of handles a surgeon must become familiar with.

Another feature of the present invention is that the end effector has an annular flange at is proximal end and the collar has a plurality of elongated cantilever fingers having hook portions for engaging the flange. The cantilever fingers are resilient to deflect radially out of the way as the flange engages and moves proximally along the hook portions, then, when the flange moves proximally past the hook portion, the fingers snap back into longitudinal alignment with the flange, securing the end effector to the collar.

In a preferred embodiment, the collar comprises an inner member supporting the cantilever fingers and an outer member. The outer member has a radially inwardly directed ridge in contacting alignment with the cantilever fingers. The ridge is configured to sufficiently deflect the cantilever fingers radially upon longitudinal movement of the outer member relative to the inner member. The hook portions are them moved out of longitudinal alignment with the flange. An advantage of this embodiment is that the collar and cantilever fingers are mounted to the handle, not the end effector. Accordingly, disposable, single use, end effectors may be made at a reduced cost. Also, the collar provides a single translational snap-on or snap-off motion that requires no additional manipulation or additional rotational motion. The collar provides an audible "click" to indicate when the end effector is attached to the handle. Thus, a user can confirm that the end effector is fully attached, and the "user friendliness" of the device is increased.

Another feature of the present invention is that the flange of the end effector has a silicone elastomer or closed cell foam affixed to it such that the elastomer or foam is compressed between the hook portions and the outer member of the collar when the end effector is secured to the collar. The elastomer or foam has several advantages in the present invention. First, the load created by the compressed elastomer or foam stabilizes the connection by removing the slop or movement due to tolerancing. Additionally, the load applied by the elastomer or foam to the collar facilitates the release and detachment of the end effector by automatically displacing the flange distally when the hook portions are disengaged from the flange, thus preventing the hook portion from re-engaging the flange.

Another feature of the invention is that the actuator includes a pivoting lever having a curved portion that defines a plurality of teeth and a head portion that engages the plunger and moves it longitudinally. A pivoting ratchet pawl is also provided to sequentially engage the teeth upon actuation of the lever. A biasing mechanism acts to bias the ratchet pawl into engagement with the teeth. A feature of the invention is that the lever includes a first extension for disengaging the ratchet pawl from the teeth upon complete actuation of the actuator and a second extension for re-engaging the ratchet pawl with the teeth upon return of the actuator to its pre-actuated position. An advantage of this embodiment is that the mechanical complexity of the ratchet and pawl mechanism is greatly reduced. It also eliminates the need for lockouts, or automatic clip feeding.

Other features and advantages of the present invention should become apparent from the following description of the drawings and detailed description of the invention and preferred embodiment of the invention.

BRIEF DESCRIPTION OF THE DRAWINGS

FIGS. 9A–9E is are cross-sectional views of the attachment, showing the plunger of the handle and the first and second actuating members of the attachment in various positions before, during, and after actuation.

DETAILED DESCRIPTION OF TEE PREFERRED EMBODIMENT

Figure 1:
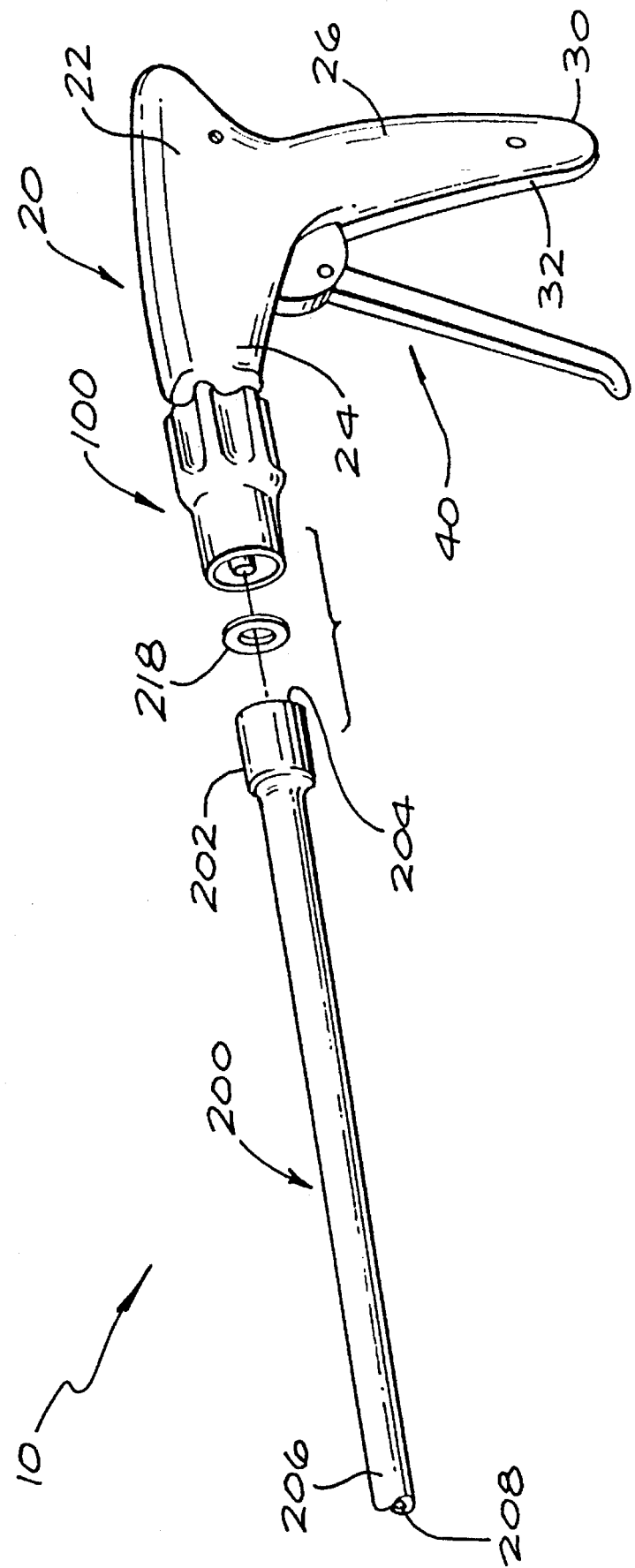
FIG. 1 is a perspective view of a surgical apparatus in accordance with the principles of the present invention, which includes an actuating handle with an attachment shown separated from the handle.

While this invention is susceptible of embodiment in various different forms, there is shown in the drawings and will.herein be described in detail a preferred embodiment of the invention. The present disclosure is to be considered an exemplification of the principles of the invention and is not intended to limit the broad aspects of the invention to the embodiment illustrated.

FIG. 1 shows a surgical instrument 10 in accordance with the principles of the present invention, that can be used in laparoscopic surgical procedures. It is appreciated that the instrument 10 is not limited to use in laparoscopic procedures, but may be used in other surgical procedures as well, e.g., endoscopic procedures and the like. The instrument 10 comprises a handle 20 having a collar 100. The apparatus 10 also includes an attachment or end effector 200, shown separated and detached from the handle 20. It is noted that the handle 20 is reusable and can be used with other kinds of disposable end effectors (not shown) of the type commonly used in laparoscopic or other surgical procedures. Such end effectors may include ligating clip appliers, staplers, disposable scissors, tackers, and the like.

Figure 2:
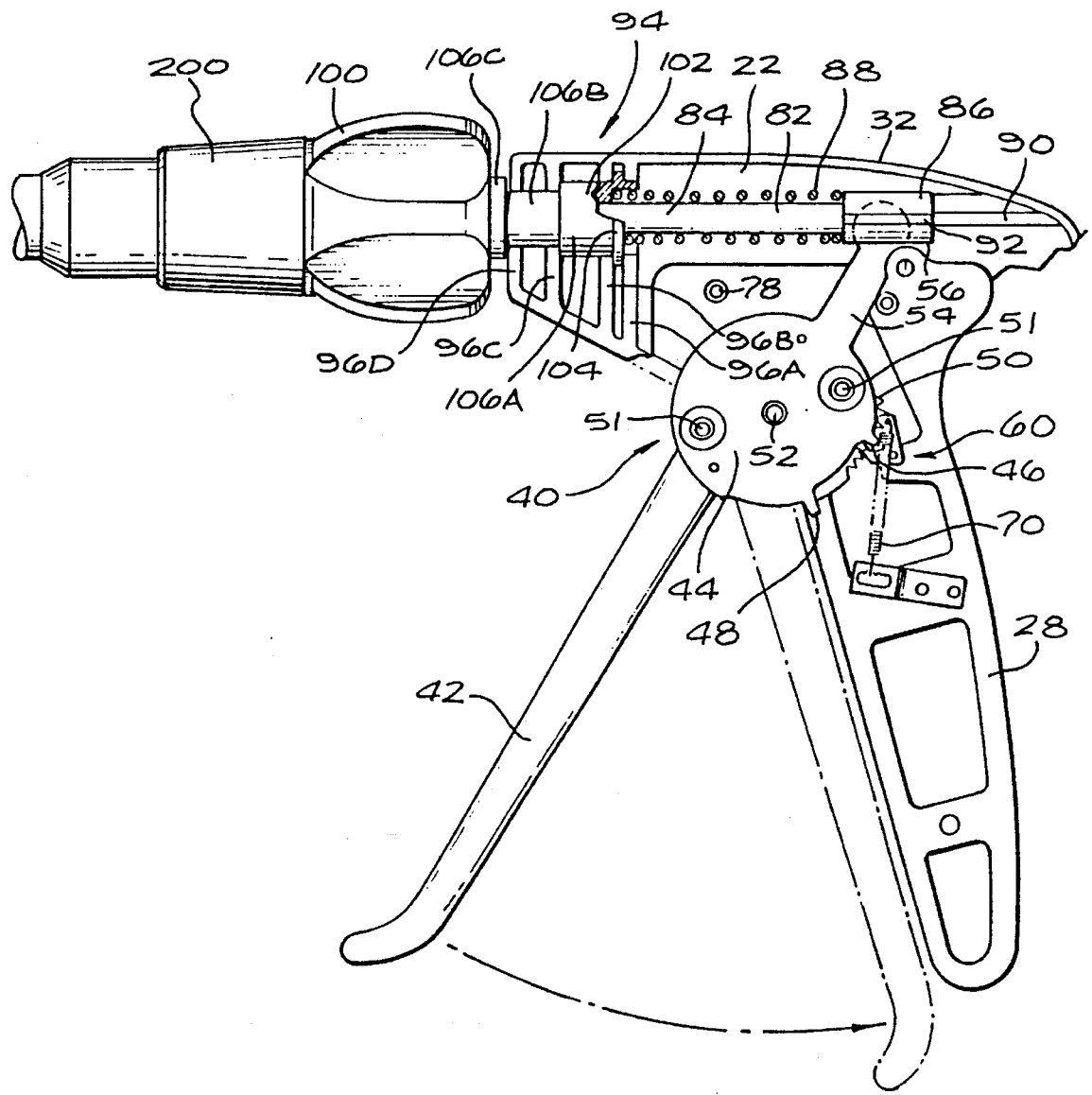
FIG. 2 is a cross-sectional view of the handle, showing the actuator and ratchet mechanism in a pre-actuated, at-rest position, and showing in phantom lines the actuator in a fully actuated position.
Figure 5:
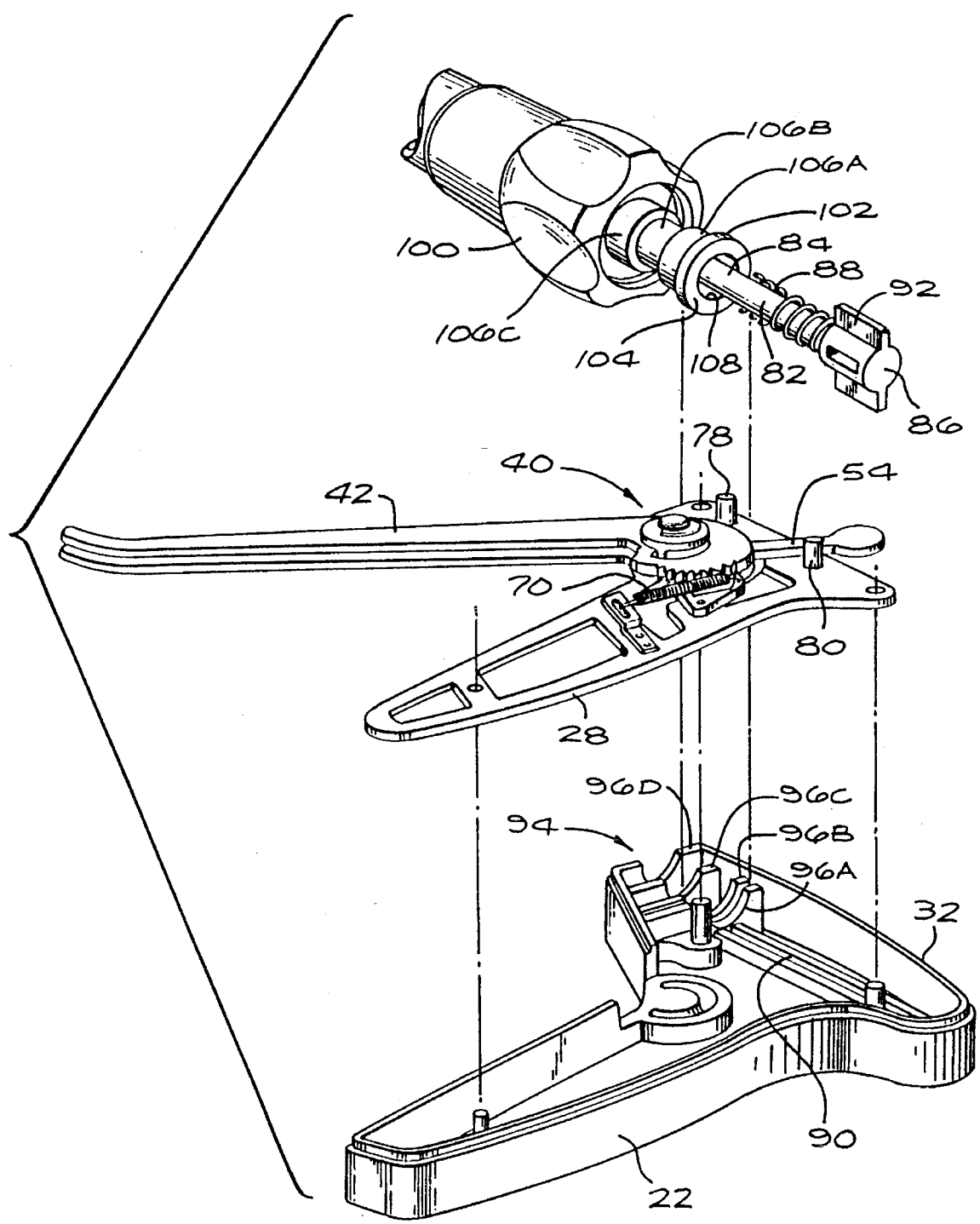
FIG. 5 is a perspective view of the internal components of the handle.

As shown in FIGS. 1, 2 and 5, the handle 20 includes an external housing 22 having an upper portion 24, a grip 26, and an internal chassis 28. The housing 22 is preferably formed of separate corresponding half sections 30, 32, made of a polycarbonate, ABS or other suitable material. The separate half sections 30, 32 may be attached together by. fasteners, welding, adhesives, or other attachment means. The chassis 28 provides a support frame for the housing 22 and a means of attachment for internal parts contained within the housing 22. The chassis 28 may be constructed of stainless steel or other suitable material. The handle 20 also includes an actuator 40 and a plunger 82.

The end effector 200 includes a proximal end 202 defining a proximal opening 204 and a distal end 206 defining a distal opening 208. The end effector 200 includes a compressible member 218, such as a silicone elastomer or a closed cell foam, that is preferably fastened to the proximal end 202, e.g., by an adhesive. The distal end 206 of the end effector 200 is typically inserted into a body cavity (not shown). The end effector 200 defines a longitudinal axis, and when assembled and in use, is mounted to the collar 100 of the handle 20 and extends distally away from the collar 100. It is contemplated and within the scope of the invention to construct the end effector 200 to be rotatable together with the collar 100 by means well known to those having ordinary skill in the art.

Referring to FIG. 2, a cross-sectional view of the handle 20 shows in solid lines the actuator 40 in a pre-actuated, at-rest position, and shows in phantom lines the actuator 40 in a fully actuated position. The range of movement of the actuator 40 is indicated by the arrow in phantom lines.

The actuator 40, as shown in FIG. 2, includes a lever 42 which extends away from the chassis 28 and is spaced a distance from the grip 26 when the actuator 40 is in the pre-actuated, at-rest condition. The actuator 40 also includes a middle portion 44 that is integrally formed with and extends from the lever 42. The middle portion 44 has a generally circular shape and includes a first extension 46, a second extension 48, and a plurality of teeth 50. The teeth 50 comprise substantially triangular-shaped ridges. In a preferred embodiment, the teeth 50 are spaced along a portion of the periphery of the middle portion 44 behind the first and second extensions 46, 48, i.e.., the teeth 50 are positioned in a different plane than the first and second extensions 46, 48. In the preferred embodiment, the middle portion 44 comprises two parts fastened together by fasteners 51 with the first part having the extensions 46, 48 and the second part having the teeth 50.

The middle portion 44 of the actuator 40 is pivotally secured to the chassis 28 by a first pivot pin 52 for pivotal movement of the lever 42 toward and away from the grip 26. The actuator 40 also includes a head portion 54 which is integrally formed with the middle portion 44 and extends upwardly from the middle portion 44. The head portion 54 is positioned within the upper portion 24 of the housing 22. In a preferred embodiment, the head portion 54 is adapted to fit within a slot 56 formed in the plunger 82.

Figure 3:
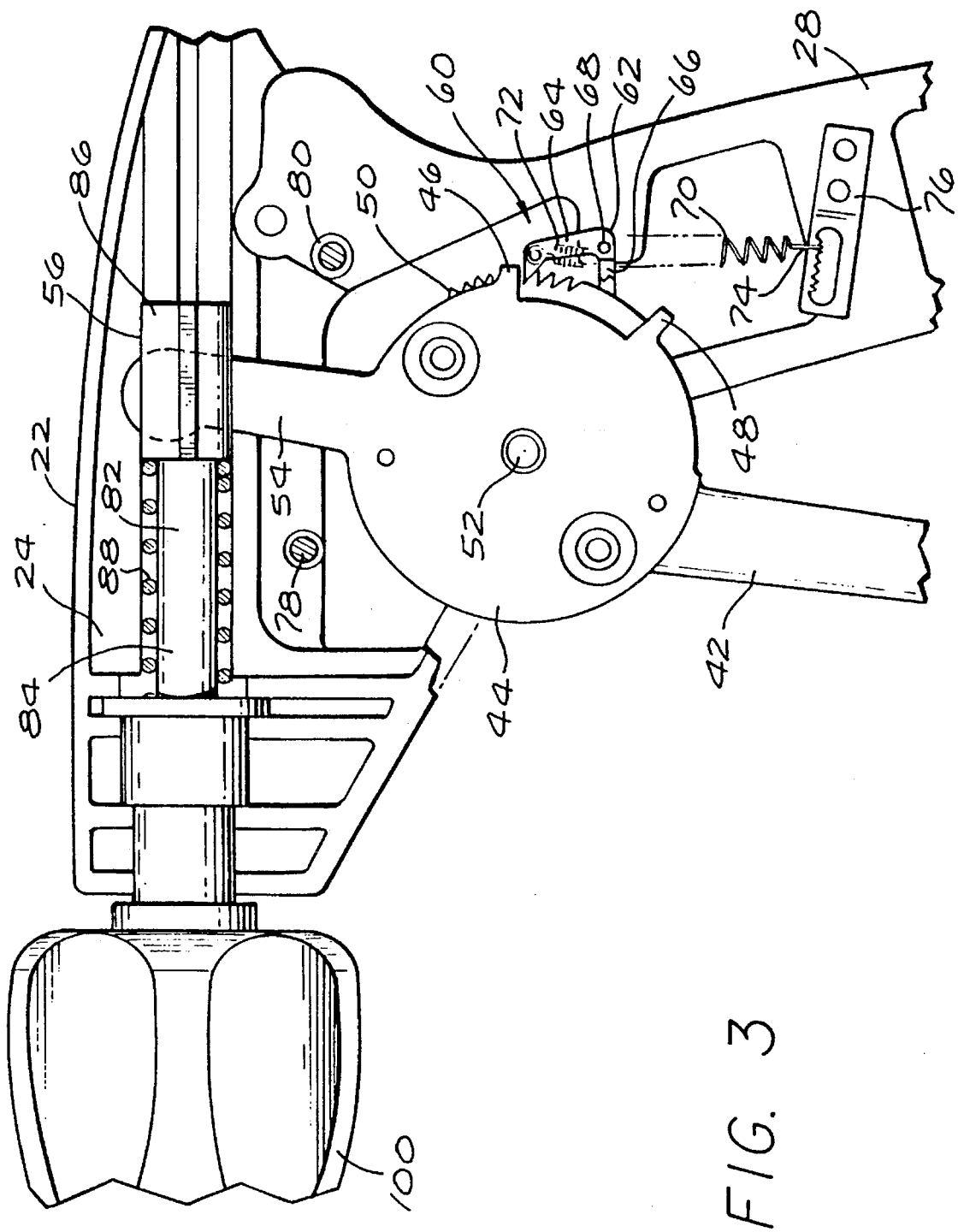
FIG. 3 is an enlarged cross-sectional view of the handle showing the actuator and ratchet mechanism of FIG. 2 in an intermediate actuated position.
Figure 4:
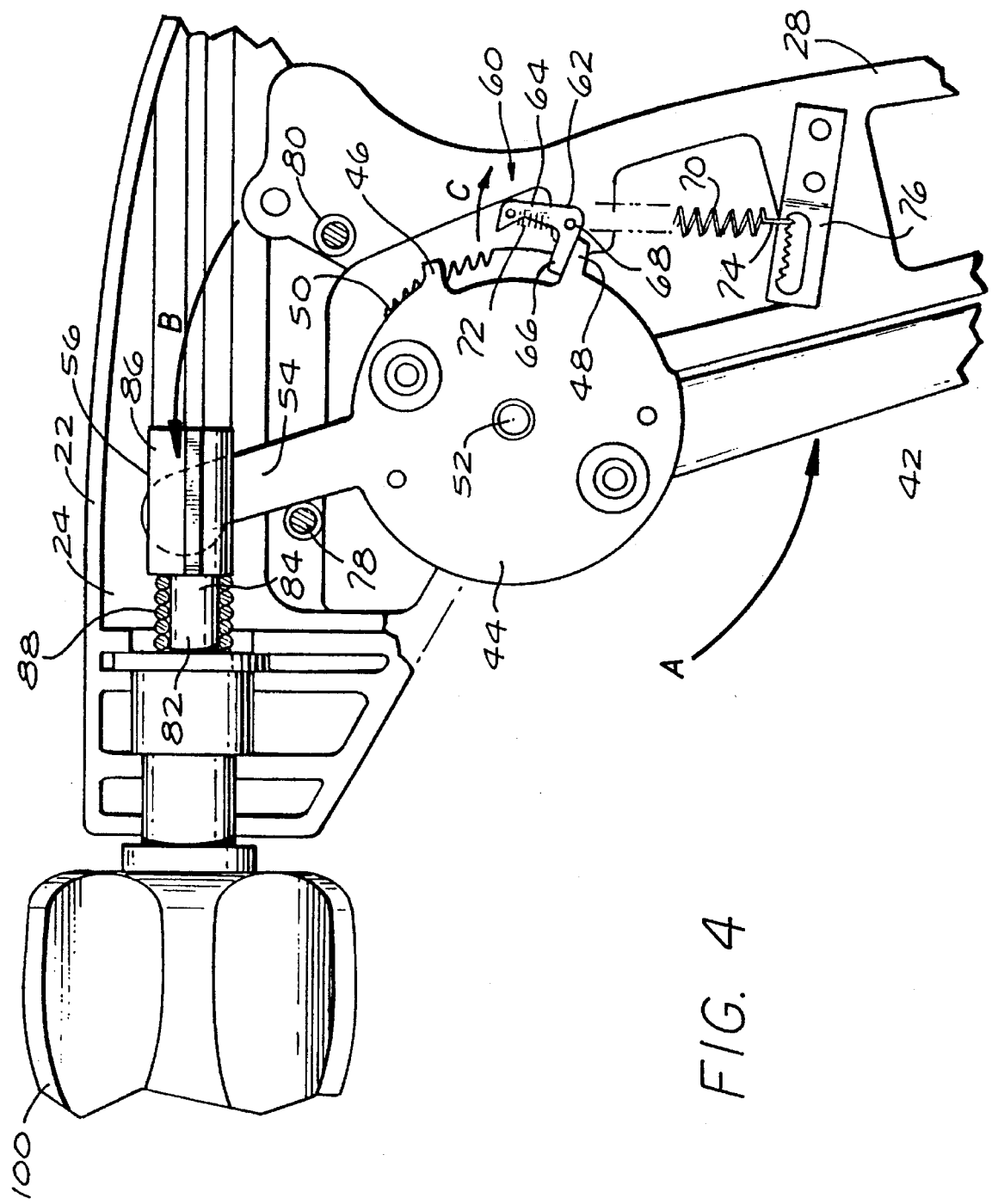
FIG. 4 is an enlarged cross-sectional view of the handle showing the actuator and ratchet mechanism of FIG. 2 in a fully actuated position.

The actuator 40 also includes a ratchet assembly 60. With reference to FIGS. 3-4, the ratchet assembly 60 includes a ratchet pawl 62 having a first leg 64 and a second leg 66. The first leg 64 and the second leg 66 are located generally perpendicular to each other but extend in different planes, such that the first leg is in the same plane as the ratchet teeth 50 and the second leg is in the same plane as the first and second extensions 46, 48. The ratchet pawl 62 is pivotally mounted to the chassis 28 of the handle 20 via a second pivot pin 68. The ratchet assembly 60 also includes a ratchet spring 70 having a top end 72 and a bottom end 74. The top end 72 of the ratchet spring 70 is preferably attached to the free end of the first leg 64 of the ratchet pawl 62. The bottom end 74 of the ratchet spring 70 may be attached to the chassis 28 or to an adjustment bracket 76 mounted on the chassis 28.

To actuate the actuator 40, a user grasps the lever 42 and squeezes it toward the grip 26 of the housing 22. Upon actuation of the actuator 40 (see FIG. 3), the first leg 64 of the ratchet pawl 62 sequentially engages and slides past each of the ratchet teeth 50. The engagement of the teeth 50 with the first leg 64 of the ratchet pawl 62 prevents the lever 42 from returning to its original position during actuation of the handle 20, in the event the lever 42 is released by the operator. Such a feature ensures proper use with a variety of possible end effectors. The ratchet pawl 62 is biased toward the teeth 50 by the resilient ratchet spring 70. The engagement of the ratchet pawl 62 with the ratchet teeth 50 provides audible confirmation that the actuator 40 is being actuated as the operator will hear a series of progressive audible clicking sounds.

FIG. 4 shows the actuator 40 and ratchet assembly 60 in a fully actuated position. The lever 42 is pulled toward the chassis 28, as shown by arrow A, until it is adjacent the chassis 28. The head portion 54 is moved distally forward, moving the plunger 82 forward, as shown by arrow B. Upon complete actuation, the actuator 40 contacts a first actuator stop 78 attached to the chassis 28. The first actuator stop 78 limits or prevents any further actuating movement by the actuator 40 in the counterclockwise direction. Upon release of the actuator 40 back to its original position, the actuator 40 contacts a second actuator stop 80 attached to the chassis 28 (see FIG. 2). The second actuator stop 80 limits or prevents any further movement by the actuator 40 in the clockwise direction. The stops 78, 80, are attached to the chassis 28 and are configured and dimensioned for specific engagement with the extending head portion 54 of the actuator 40 in a manner to thereby limit the pivotal movement of the actuator 40 in both directions.

Referring again to FIG. 4, upon complete actuation of the actuator 40, the second extension 48 engages the second leg 66 of the ratchet pawl 62, so that the ratchet pawl 62 pivots in a clockwise direction, as indicated by arrow C. The ratchet spring 70 is thus moved over the pivot center of the ratchet pawl 62, the pivot center being that point where the second pivot pin 68 is mounted. The movement of the ratchet spring 70 over center prevents the first leg 64 of the ratchet pawl 62 from engaging the ratchet teeth 50. The actuator 40 can then freely return to its original position. Upon release of the lever 42 back to its original pre-actuated position, the first extension 46 engages the second leg 66 of the ratchet pawl 62 and pivots the ratchet pawl 62 in a counterclockwise direction back to its original position, so that the first leg 64 is again in a position to engage the teeth 50 (see FIG. 2). Thus, the actuating mechanism of the present invention allows an operator to squeeze the lever 42 toward the grip portion 26 while maintaining all intermediate positions, in the event the operator releases the lever prior to completion of the stroke. Then, once the lever has been fully actuated, the ratchet pawl is disengaged and the operator is free to move the lever through all positions between the at-rest position and the fully actuated position.

Referring still to FIGS. 2-4, the plunger 82 is shown in various stages of actuation. The plunger 82 includes a longitudinally extending rod 84 and a support member 86 at the proximal end of the rod. The support member 86 has the slot 56 for receiving the head portion 54 of the actuator 40. The plunger 82 is axially oriented to both the collar 100 and the end effector 200 and is capable of moving axially and longitudinally through the interior of both the collar 100 and the end effector 200. Upon actuation of the handle 20, the actuator 40 engages the plunger 82 and moves it distally forward. Upon complete actuation and subsequent release of the actuator 40, a plunger spring 88 urges the plunger 82 back to its original position With reference to FIGS. 2 and 5, the assembly of the housing 22, the actuator 40, the plunger 82 and the collar 100 will now be further described. In that the housing includes two symmetrical half sections 30, 32, only the half section 32 will be described, it being appreciated that the half section 30 is of the same construction. The half section 32 includes a longitudinal slot 90 for locating a wing 92 of the support member 86 of the plunger 82, thus permitting the plunger 82 to be guided longitudinally within the handle. The half section 32 also includes a mount 94 for supporting an inner member 102 of the collar 100. The mount includes four transverse walls 96 A, B, C, D for cradling the inner member 102 of the collar 100. In particular, the inner member has a flange 104 that is located between the first and second transverse walls 96A, B to prevent longitudinal movement of the inner member. The inner member also includes three cylindrical portions 106A, B, C, with cylindrical portion 106B having a smaller diameter than cylindrical portions 106A, C. Cylindrical portion 106B is cradled by notches in transverse walls 96C, D. Preferably, cylindrical portions 106A, C engage the transverse walls 96C, D to further prevent longitudinal movement of the inner member 102 of the collar.

The inner member 102 of the collar also has an opening 108 therethrough for receiving the plunger 84. A snap ring (not shown) may be fixed to the plunger to prevent separation of the plunger from the inner member 102 during assembly of the remainder of the instrument.

With reference to FIG. 5, it should be appreciated that the handle 20 has a modular construction that facilitates cleaning and replacement of individual components. In particular, the half sections 30, 32, the chassis 28 and actuator 40, the plunger 82 and the collar 100 may all be easily disassembled from each other and cleaned.

Figure 6:
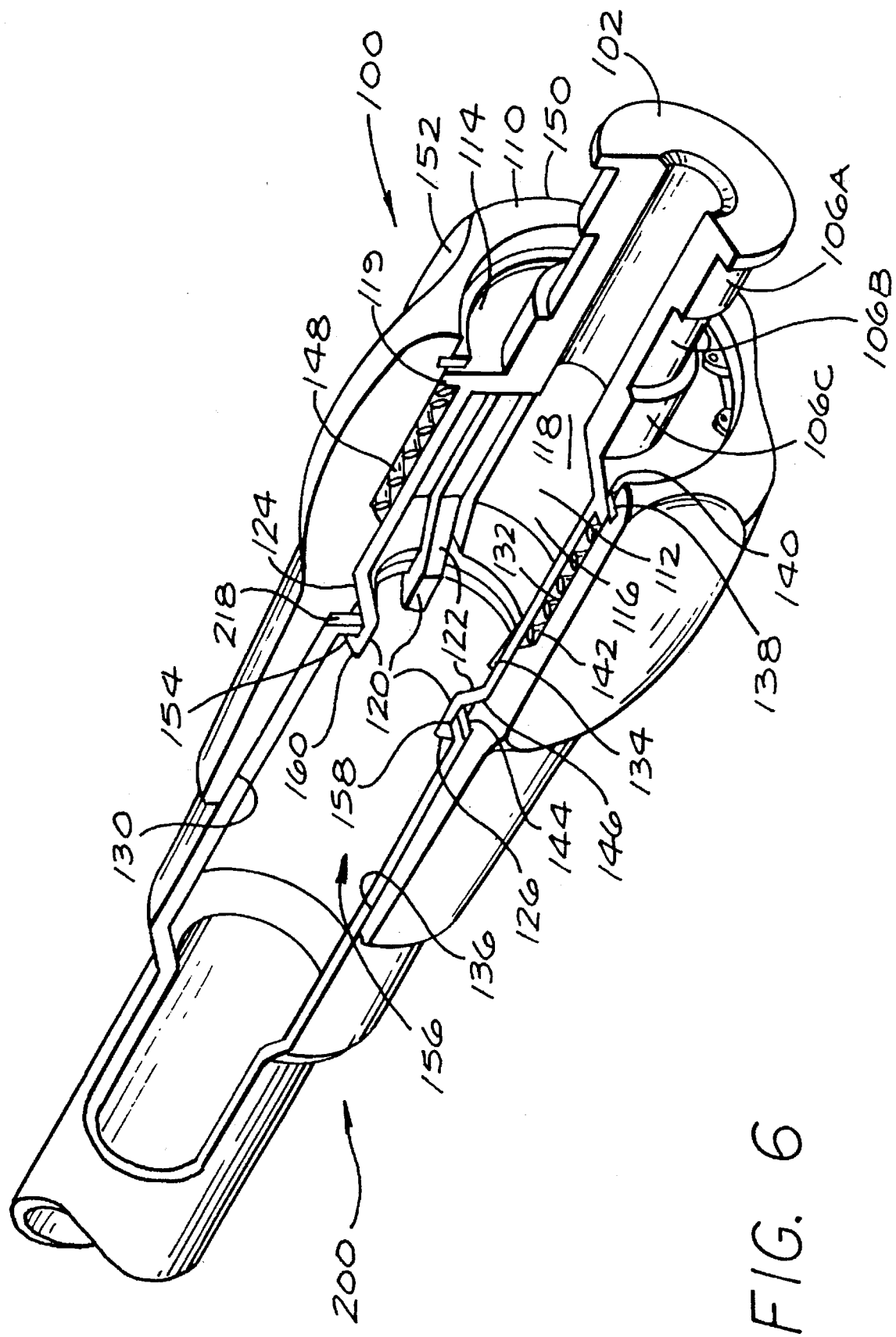
FIG. 6 is a partial perspective cut-away view showing the attachment in a position attached to the handle.
Figure 7:
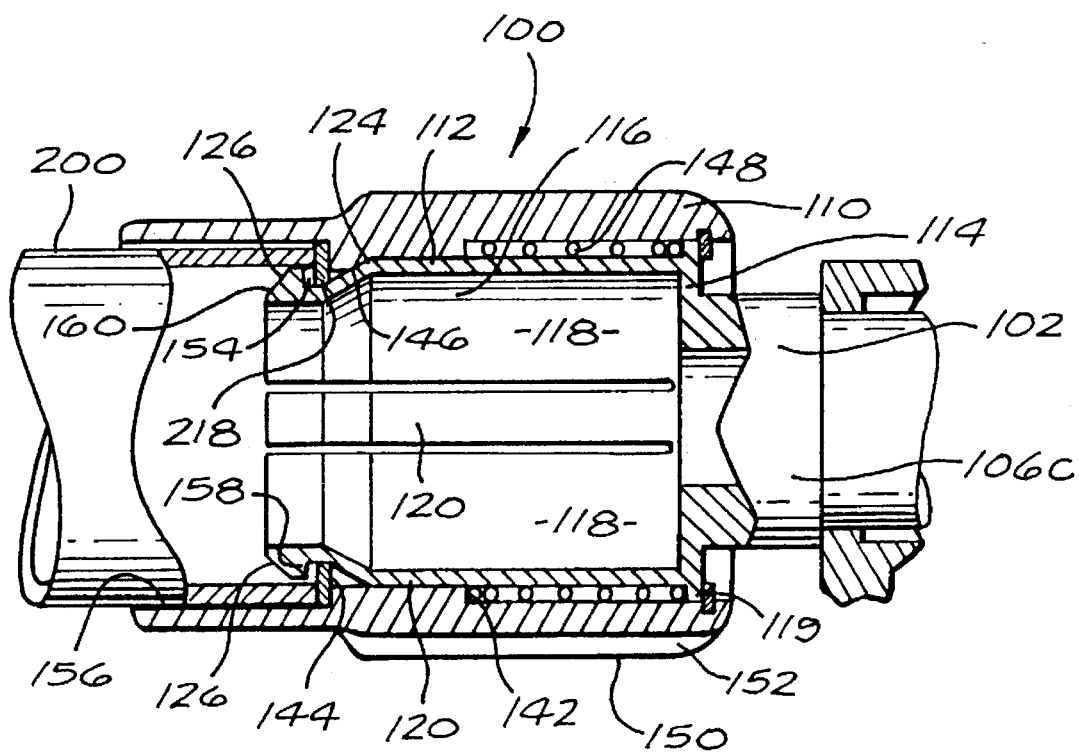
FIG. 7 is an enlarged cross-sectional view showing the attachment between the handle and the proximal end portion of the attachment.
Figure 8:
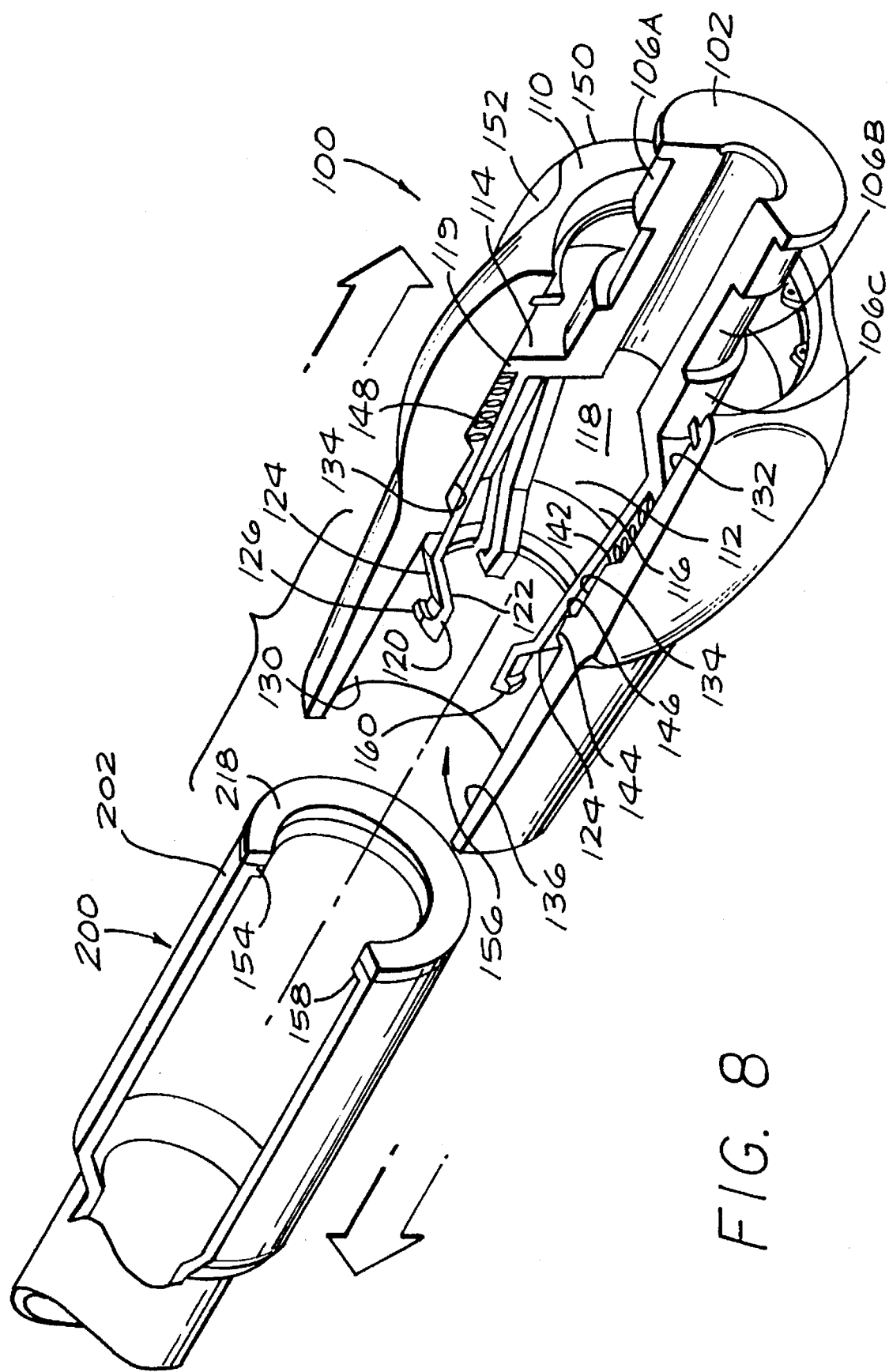
FIG. 8 is a partial perspective cut-away view showing the attachment in a position detached from the handle.

With reference to FIGS. 6-8, the collar 100 and the means for attaching the end effector 200 to the collar 100 will now be described. The collar 100 is substantially cylindrical in shape and defines a longitudinal axis. The collar 100 provides a connection between the proximal end 202 of the end effector 200 and the handle 20. The collar 100 of the present invention can be used with a variety of conventional end effectors of the type commonly used in laparoscopic surgical procedures. Such end effectors may include ligating clip appliers, staplers, disposable scissors, tackers, and the like, and is not limited to use with one specific end effector. The end effectors may be disposed of after each use. The collar 100 provides the user with the ability to attach and detach an end effector to a handle with a single translational snap-on or snap-off motion and without the need for additional rotational motions. The preferred embodiment of the present invention includes a collar 100 that provides a connection between a disposable laparoscopic end effector and a reusable laparoscopic handle.

The collar 100 includes the inner member 102, referred to above, and an outer member 110. The inner member 102 also includes a barrel portion 112 that is located within the outer member 110 distally of the third cylindrical portion 106C. The barrel portion includes an end wall 114 and a generally cylindrical, longitudinally extending, wall 116 formed from four spaced apart arcuate portions 118. The end wall 114 has a greater diameter than the cylindrical wall so as to form an annular shoulder 119 that supports an end of a spring 148, which will be described in more detail later.

Extending longitudinally and distally from the end wall 114 are four cantilever fingers 120. Each cantilever finger is located in the space between adjacent arcuate portions. Preferably, the arcuate portions assist in supporting the fingers in the circumferential direction. It will be appreciated upon a further discussion of the operation of the cantilever fingers, that more or less than four fingers may be used and that the arcuate portions may be closely adjacent the fingers or omitted entirely.

Each cantilever finger has a mid-section 122 that projects radially inwardly and distally to form a ramp surface 124. At the distal end of the ramp surface, the finger projects distally, then radially outwardly and proximally to form a hook portion 126 at a distal end 128 of the finger. The fingers are resilient so as to be flexible radially inwardly from their normal or at rest position. The fingers also have memory and return to their rest positions when the flexing force is released. The inner member of the collar is preferably made of stainless steel, including the fingers which are dimensioned to provide the desired resilient properties.

The outer member 110 of the collar includes an interior annular surface 130 defining a proximal wall 132, a mid-wall 134 and a distal wall 136. The proximal wall has an annular groove 138 formed therein to receive a snap ring 140 to prevent separation of the outer member from the inner member after assembly. The mid-wall has a smaller diameter than. the proximal wall, forming a shoulder 142. Between the mid-wall and distal wall is an annular ridge 144 having a ramp surface 146 configured to engage the ramp surface 124 of the inner member 102 upon relative longitudinal movement of the inner and outer members. A collar spring 148 is located radially between the inner and outer members and is biased between the shoulder 142 of the outer member and the shoulder 119 of the inner member so as to urge the outer member distally relative to the inner member. Preferably, an outer surface 150 of the outer member 110 has a plurality of radial protrusions 152 to facilitate the gripping and pulling of the outer member 110 toward the handle 20.

Next, the procedure for attaching and detaching the end effector to and from the collar will be described. With reference again to FIGS. 6–8, it is seen that the proximal end 202 of the end effector has a radially inwardly directed annular flange 154 onto which is affixed the compressible member 218. To attach the end effector to the collar, a user simply inserts the proximal end 202 of the end effector into an opening 156 at the distal end of the collar until the compressible member 218 or flange 154 contacts the hook portions 126 of the cantilever fingers 120. Further proximal movement of the end effector 200 results in the hook portions 126 deflecting radially inwardly until the end effector is inserted sufficiently to permit the hook portions to snap over an interior edge 158 of the annular flange 154, at which point the hook portions return to their undeformed positions. This movement and subsequent snapping of the cantilever fingers 120 against the annular flange 154 of the end effector provides an audible "click" to indicate to the user that the end effector 200 is securely attached to the collar 100.

In the preferred embodiment, the hook portions 126 have angled faces 160 upon which the annular flange 154 of the end effector rides, causing the flexing of the hook portions. It will be appreciated, however, that the annular flange may have the angled face and the hook portions would then ride along the angled face of the flange until passing over the interior edge 158 of the flange and snapping back to their undeformed positions.

In the preferred embodiment, the elastomer or closed cell foam portion 218 is compressed between the annular ridge 144 of the outer member 110 of the collar and the hook portions 126 of the cantilever fingers 120 to create a load (see FIG. 7). This provides a firm connection with no slop or looseness and also automatically ejects the end effector 200 from the collar 100 when it is desired to detach the end effector, as will be described below.

With reference to FIG. 8, the end effector 200 is detached from the collar 100 by pulling the outer member 110 of the collar proximally against the force of the spring 148. This causes the ramp surface 146 on the annular ridge 144 of the outer member 110 to interface the ramp surfaces 124 of the cantilever fingers 120, causing the fingers to deflect radially inwardly. When the fingers are flexed sufficiently inwardly to permit the hook portions 126 to clear the interior edge 158 of the flange, the compressible member 218 will expand, pushing the end effector 200 distally a sufficient distance to prevent re-engagement of the fingers 120 to the annular flange 154. The user may then release the outer member 110, which returns to its original position due to the biasing force of the spring, and remove the end effector from the collar or simply allow gravity to let the end effector fall out of the distal opening 156 of the collar.

It can be seen from the above that the collar 100 of the present invention allows a user to attach the end effector 200 to the collar 100 with a single translational snap-on motion that requires no additional manipulation, such as a rotational movement. The end effector can also be detached using one hand. For example, when the instrument is resting on a table, a user may press the palm of the hand on the handle 20 and pull the collar 100 toward the palm with the fingers of the same hand. As noted above, the end effector will eject from the collar due to the expansion force of the compressible member.

It will be appreciated that the specific connection mechanism described above may be varied in many ways and yet obtain the benefits taught herein. Alternative embodiments could vary the location of the end effector flange, the cantilever fingers and the ramp surfaces.

With the end effector attached to the collar, the surgical instrument may now be actuated to perform its intended function or functions. With reference to FIG. 9A, the end effector 200 is actuated by the longitudinal movement of the plunger 82 through the collar 100 into engagement with an actuating member 304 or actuating members 304,306 associated with the end effector. In the preferred embodiment, the end effector 200 includes an outer support tube 302, the first actuating member 304, the second actuating member 306, a spring support 308 and first and second actuating member springs 310, 312. The outer tube is preferably made from ABS or polycarbonate.

The first actuating member 304 includes a distal portion 314 and a proximal portion 316. The distal portion is concentrically located inside the outer support tube and has a first cylindrical portion 318 and a second cylindrical portion 320 located proximally thereto. The second cylindrical portion has a larger diameter than the first cylindrical portion, thus forming an annular wall 321 for engaging one end of the first actuating member spring 310.

The proximal portion 316 of the first actuating member 304 includes a bearing portion 322 and a deflectable portion 324. The bearing portion is proximal to and integral with the second cylindrical portion 320. Preferably, the bearing portion has a half-cylinder shape, an outer surface 326 of which conforms to and bears against an inside surface 328 of the outer support tube 302. Preferably, the deflectable portion 324 is in the form of a cantilever that is integral to and extends proximally from the bearing portion. The cantilever may have a partial cylindrical shape wherein an outer wall 332 of the cantilever is spaced from the inside surface 328 of the outer support tube 302. A proximal end 334 of the cantilever has a radially inwardly disposed lip 336 that is located in contacting alignment with the distal end of the plunger 82 upon movement of the plunger in a distal direction.

The first actuating member 304 is preferably made of ABS or polycarbonate. The cantilever may be made of the same material, but is dimensioned to provide resiliency such that the unsupported proximal end 334 of the cantilever may be flexed radially outward, yet return to its original position in the absence of the flexing force.

The second actuating member 306 includes a distal portion 338 and a proximal portion 340. The distal portion has a split tube portion 342 and a larger diameter, tubular portion 344 located proximally thereto, forming an annular wall 346 for engaging one end of the second actuating member spring 312. The distal portion of the second actuating member is concentrically located inside the outer support tube 302 with the first cylindrical portion 318 of the first actuating member 304 passing inside and through the split tube portion 342 of the second actuating member 306.

The proximal portion 340 of the second actuating member 306 is proximal to and integral with the tubular portion 344 and, preferably, has a half-cylinder shape, an outer surface 348 of which bears against the inside surface 328 of the outer support tube 302. It will be appreciated that the half-cylinder shape of the bearing portion 322 of the first actuating member and the half-cylinder shape of the proximal portion 340 of the second actuating member may be located in opposed relationship to each other to form a sliding surface 350, permitting relative movement between them.

The half-cylindrical proximal portion 340 of the second actuating member includes a transverse wall 352 that extends radially inwardly. The traverse wall is located distally of a proximal end 354 of the proximal portion and, preferably, includes a ramp surface 356 at its radially inward end. The ramp surface is located in contacting alignment with the lip 336 of the cantilever 324 upon movement of the first actuating member 304 in the distal direction. The second actuating member 306 is preferably made of ABS, polycarbonate, or other suitable material.

Figure 10:
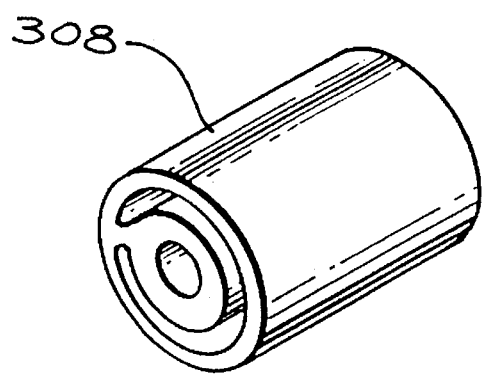
FIG. 10 is a perspective view of the spring support shown in FIGS. 9A–9E.

With reference also to FIG. 10, the spring support 308 is fastened to the inside surface 328 of the outer support tube, e.g., by welding, fasteners or adhesive, or may be molded with the outer support tube. The spring support may be made of metal, plastic or other suitable material. The spring support defines a central bore 358 for receiving the first cylindrical portion 318 of the first actuating member and one or more arcuate slots 360 for receiving the split tube portion 342 of the second actuating member. The first actuating member spring is located around the first cylindrical portion of the first actuating member and is biased between the annular wall 321 of the first actuating member and the spring support. The second actuating member spring is located around the split tube portion 342 of the second actuating member and is biased between the annular wall 346 of the second actuating member and the spring support. Because the spring support is fixed to the outer support tube, both the first and second actuating member springs will urge the first and second actuating members proximally.

Figure 9E:
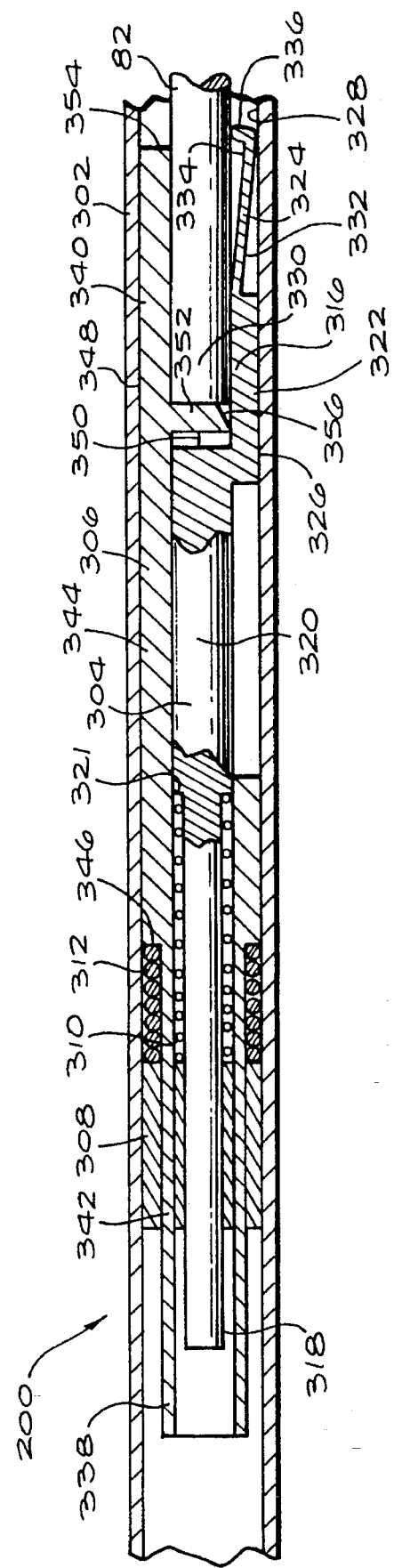

The actuation of the end effector will now be described with respect to FIGS. 9A–9E. FIG. 9A shows the plunger 82, the first actuating member 304 and the second actuating member 306 in their original, pre-actuated positions. The first actuating member 304 is mounted for longitudinal movement within the outer support tube 302 and is in contacting longitudinal alignment with a distal end 330 of the plunger 82. When the lever portion 42 of the actuator 40 is squeezed toward the grip 26 (see FIG. 2), the plunger 82 moves distally forward, and the distal end 330 of the plunger 82 engages the proximal end 334 of the deflectable portion 324 of the first actuating member 304 and moves the first actuating member 304 distally forward a desired distance. For example, in a clip applier, the desired distance traveled by the first actuating member 304 is a distance sufficient to advance a clip (not shown) into the jaws of the clip applier.

With reference to FIG. 9B, the plunger 82 moves the first actuating member 304 to a position where the lip 336 of the deflectable portion 324 engages the ramp 356 of the transverse wall 352 of the second actuating member 306. The lip 336 and the transverse wall 352 are positioned in contacting alignment relative to each other and are configured, such that distal movement of the plunger 82 results in their engagement.

With reference to FIG. 9C, further distal movement of the plunger 82 results in the lip 336 sliding down the ramp 356, causing the proximal end 334 of the deflectable portion 324 to move radially outwardly and out of longitudinal alignment with the plunger 82. Specifically the lip 336 moves against the ramp surface 356 until it is forced below the ramp surface 356, disengaging the deflectable portion from the distal end 330 of the plunger 82. At this point, the spring force of the first actuating member spring 310 urges the first actuating member 304 proximally to its original starting position (see FIG. 9D).

Referring to FIG. 9D, the first actuating member 304 is shown disengaged from the plunger 82 and moved radially out of the way, with the transverse wall 352 of the second actuating member 306 now in contacting longitudinal alignment with the distal end 330 of the plunger 82. With reference to FIG. 9E, the distal end 330 of the plunger 82 engages the transverse wall 352 of the actuator 306 and moves it distally a desired distance. For example, in a clip applier, the desired distance traveled by the second actuating member 306 is a distance sufficient to engage and close the jaws (not shown) of the clip applier.

Once the second actuating member 306 has been moved the sufficient distance, the actuator 40 may be released and the plunger 82, the deflectable portion 324 of the first actuating member 304, and the second actuating member 306 returned to their original starting positions. In particular, the plunger spring retracts the plunger into the handle, the second actuating member spring 312 urges the second actuating member back to its original starting position and the deflectable portion 324 flexes back into longitudinally contacting alignment with the plunger 82 (see FIG. 9A).

Thus, the surgical apparatus 10 of the present invention includes a universal handle 20 that can be used with a variety of different end effectors, including single action end effectors that perform a single function and double action end effectors that perform two functions. The surgical instrument includes an actuator 40 that converts a single plunger motion into two separate and independent actuator motions required for actuating a first actuating member 304 and a second actuating member 306. A ratcheting assembly 60 is also provided that locks the instrument in successive positions during actuation, but frees the actuator once the end effector operation has been completed. Finally, an easy to use attachment mechanism is provided for securely and quickly attaching and detaching the disposable end effectors.

While the invention has been described with reference to preferred embodiments, it will be understood by those skilled in the art that various changes may be made and equivalents may be substituted for elements thereof without departing from the broader aspects of the invention. Also, it is intended that broad claims not specifying details of a particular embodiment disclosed herein as the best mode contemplated for carrying out the invention, should not be limited to such details. Therefore, the above description should not be taken as limiting the scope of the invention which is defined by the appended claims.

What is claimed is:

1. A surgical apparatus comprising:

a handle;

an end effector defining a longitudinal axis mounted to the handle and extending distally therefrom;

a plunger mounted to the handle in axial alignment with the longitudinal axis of the end effector, the plunger being longitudinally movable within the end effector;

an actuator engageable with the plunger for moving a distal end of the plunger longitudinally;

a first actuator member mounted for longitudinal movement within the end effector and engageable by the distal end of the plunger, wherein upon actuation of the actuator, the distal end of the plunger moves the first actuating member distally; and, a second actuating member mounted for longitudinal movement within the end effector and engageable by the distal end of the plunger, the second actuating member being sequentially engaged by the plunger after the plunger moves the first actuating member distally.

2. The apparatus of claim 1, wherein the first actuating member includes a deflectable portion and the second actuating member includes a transverse wall, the deflectable portion and the transverse wall positioned in contacting alignment relative to each other and configured such that distal movement of the first actuating member results in the transverse wall urging the deflectable portion out of longitudinal alignment with the plunger.

3. The apparatus of claim 2, wherein the deflectable portion is a cantilever with a lip and the transverse wall has a ramped surface, and wherein the first actuating member is moved out of longitudinal alignment with the plunger due to the interaction between the lip and the ramped surface during distal movement of the first actuating member.

4. The apparatus of claim 3, further comprising a first actuating member spring that urges the first actuating member proximally when the first actuating member is moved out of longitudinal alignment with the plunger.

5. The apparatus of claim 4, wherein the cantilever is resilient such that it returns to its preactuated position when the plunger returns to its preactuated position.

6. The apparatus of claim 1, wherein the end effector includes an outer support tube, the first actuating member includes a longitudinally extending cantilever at its proximal end engageable by the distal end of the plunger, and the second actuating member includes a transverse wall, the cantilever and the transverse wall positioned to be engageable with each other and configured such that distal movement of the first actuating member results in the transverse wall urging the cantilever out of longitudinal alignment with the distal end of the plunger.

7. The apparatus of claim 1, wherein the surgical apparatus comprises a collar mounted to the handle.

8. The apparatus of claim 7, wherein the end effector and the first and second actuating members are a disposable loading unit that is releasably attachable to the collar.

9. The apparatus of claim 8, wherein the disposable loading unit is one of a plurality of disposable loading units that perform different functions, each of said plurality being operable by the plunger.

10. The apparatus of claim 9, wherein one of the plurality of disposable loading units is a single action end effector.

11. The apparatus of claim 7, wherein the end effector has an annular flange at its proximal end and the collar has an elongated cantilever finger having a hook portion at its distal end, the cantilever finger being engageable with the flange of the end effector when the end effector is inserted longitudinally into the collar, the cantilever finger being resilient to deflect radially out of the way as the flange engages and moves proximally along the hook portion, then snap back into longitudinal alignment with the flange, securing the end effector to the collar, when the flange moves proximally past the hook portion.

12. The apparatus of claim 11, wherein the collar comprises an inner member and an outer member with the inner member mounted to the handle and the outer member mounted to and longitudinally movable relative to the inner member, the inner member having the cantilever finger and the outer member having a radially inwardly directed ridge in contacting alignment with the cantilever finger and configured to sufficiently deflect the cantilever finger radially, upon longitudinal movement of the outer member relative to the inner member, to move the hook portion out of longitudinal alignment with the flange.

13. The apparatus of claim 12, further comprising a compressible member affixed to the proximal side of the flange of the end effector, the compressible member configured to be compressed between the hook portion and the outer member of the collar when the end effector is secured to the collar.

14. The apparatus of claim 13, further comprising a spring radially located between the inner and outer members of the collar to urge the ridge of the outer member out of engagement with the cantilever finger.

15. The apparatus of claim 14, wherein the ridge of the outer member is in contacting alignment with a ramp portion of the cantilever finger for moving the hook portion out of longitudinal alignment with the flange.

16. The apparatus of claim 1, wherein the actuator comprises:

a lever pivotally mounted to the handle, the lever having a curved portion and a head portion, the curved portion defining a plurality of teeth and the head portion configured to engage the plunger and move the distal end of the plunger longitudinally upon actuation of the lever in a first direction;

a ratchet pawl pivotally mounted to the handle, the ratchet pawl having a first leg for sequentially engaging the teeth upon actuation of the lever in the first direction; and a biasing mechanism to bias the first leg of the ratchet pawl into engagement with the teeth when the lever is actuated in the first direction.

17. The apparatus of claim 16, wherein the lever further comprises a first extension for disengaging the first leg from the teeth upon continued actuation of the actuator in the first direction.

18. The apparatus of claim 17, wherein the lever further comprises a second extension for reengaging the first leg with the teeth upon return of the actuator to its pre-actuated position.

19. The apparatus of claim 18, wherein the ratchet pawl includes a second leg mounted to and generally perpendicular to the first leg, the first and second extensions engaging the second leg for disengaging and reengaging the first leg and the teeth.

20. The apparatus of claim 19, wherein the teeth and the first leg are in a first plane and the first and second extensions and the second leg are in a second plane parallel to the first plane.

21. The apparatus of claim 18, wherein the biasing mechanism is a spring having one end fixed to the ratchet pawl and the other end fixed to the handle.

22. The apparatus of claim 21, wherein the plurality of teeth protrude radially in relation to the lever pivot.

23. The apparatus of claim 1 further comprising a plunger spring mounted around the proximal end of the plunger for biasing the plunger in a retracted position.

24. A surgical apparatus comprising:

a handle;

a collar mounted to the handle;

an end effector defining a longitudinal axis mounted to the collar and extending distally therefrom;

a plunger mounted to the handle in axial alignment with the longitudinal axis of the end effector, the plunger being longitudinally movable within the end effector; and an actuator engageable with the plunger for moving a distal end of the plunger longitudinally to operate the end effector;

wherein the end effector has an annular flange at its proximal end and the collar has an elongated cantilever finger having a hook portion at its distal end, the cantilever finger being engageable with the flange of the end effector when the end effector is inserted longitudinally into the collar, the cantilever finger being resilient to deflect radially out of the way as the flange engages and moves proximally along the hook portion, then snap back into longitudinal alignment with the flange, securing the end effector to the collar, when the flange moves proximally past the hook portion.

25. The apparatus of claim 24, wherein the collar comprises an inner member and an outer member with the inner member mounted to the handle and the outer member mounted to and longitudinally movable relative to the inner member, the inner member having the cantilever finger and the outer member having a radially inwardly directed ridge engageable with the cantilever finger and configured to sufficiently deflect the cantilever finger radially, upon longitudinal movement of the outer member relative to the inner member, to move the hook portion out of longitudinal alignment with the flange.

26. The apparatus of claim 25, further comprising a compressible member affixed to the proximal side of the flange of the end effector, the compressible member configured to be compressed between the hook portion and the outer member of the collar when the end effector is secured to the collar.

27. The apparatus of claim 26, further comprising a spring radially located between the inner and outer members of the collar to urge the ridge of the outer member out of engagement with the cantilever finger.

28. The apparatus of claim 27, wherein the ridge of the outer member is engageable with a ramp portion of the cantilever finger for moving the hook portion out of alignment with the flange.

29. The apparatus of claim 28, wherein there is a plurality of said cantilever fingers, circumferentially arranged within the outer member, said ridge of said outer member located to be engageable with the ramps of each of said plurality of cantilever fingers.

30. A surgical apparatus comprising:

a handle;

a collar mounted to the handle;

an end effector defining a longitudinal axis mounted to the collar and extending distally therefrom;

a plunger mounted to the handle in axial alignment with the longitudinal axis of the end effector, the plunger being longitudinally movable within the end effector; and an actuator engageable with the plunger for moving a distal end of the plunger longitudinally;

wherein the actuator comprises:

a lever pivotally mounted to the handle, the lever having a curved portion and a head portion, the curved portion defining a plurality of teeth and the head portion configured to engage the plunger and move the distal end of the plunger longitudinally upon actuation of the lever in a first direction;

a ratchet pawl pivotally mounted to the handle, ratchet pawl having a first leg for sequentially engaging the teeth upon actuation of the lever in the first direction; and a biasing mechanism to bias the first leg of the ratchet pawl into engagement with the teeth when the lever is actuated in the first direction.

31. The apparatus of claim 30, wherein the lever further comprises a first extension for disengaging the first leg from the teeth upon continued actuation of the actuator in the first direction.

32. The apparatus of claim 31, wherein the lever further comprises a second extension for reengaging the first leg with the teeth upon return of the actuator to its pre-actuated position.

33. The apparatus of claim 32, wherein the ratchet pawl includes a second leg mounted to and generally perpendicular to the first leg, the first and second extensions engaging the second leg for disengaging and reengaging the first leg and the teeth.

34. The apparatus of claim 33, wherein the teeth and the first leg are in a first plane and the first and second extensions and the second leg are in a second plane parallel to the first plane.

35. The apparatus of claim 34, wherein the biasing mechanism is a spring having one end fixed to the ratchet pawl and the other end fixed to the handle.

36. The apparatus of claim 35, wherein the plurality of teeth protrude radially in relation to the lever pivot.

* * * * *